United States Patent [19]

Baudet

[11] 4,276,421

[45] Jun. 30, 1981

[54] CYANO-GUANIDINE GEOMETRICAL ISOMERS

[75] Inventor: Pierre Baudet, Geneva, Switzerland

[73] Assignee: Société de Recherches et de Syntheses Organiques S.A., Geneva, Switzerland

[21] Appl. No.: 94,660

[22] Filed: Nov. 15, 1979

[30] Foreign Application Priority Data

Nov. 18, 1978 [CH] Switzerland .................. 11810/78

[51] Int. Cl.$^3$ .................. C07D 233/64; C07C 129/08; C07D 203/06
[52] U.S. Cl. ........................... 548/342; 260/239 E; 564/240; 423/368
[58] Field of Search .............. 548/342; 260/239 E, 260/564 A; 564/240

[56] References Cited

U.S. PATENT DOCUMENTS

| | | | |
|---|---|---|---|
| 4,013,678 | 3/1977 | Brown et al. | 548/342 |
| 4,049,671 | 9/1977 | Durant et al. | 548/342 |
| 4,049,672 | 9/1977 | Durant et al. | 548/342 |

OTHER PUBLICATIONS

Bruzzi et al. Chem. Abst. 90:103960a.
Lab. Estedi Chem. Abst. 91:175354z.
Kamiya et al. Chem. Abst. vol. 78, 1973, 42830m.

*Primary Examiner*—Henry R. Jiles
*Assistant Examiner*—Jane T. Fan
*Attorney, Agent, or Firm*—Pennie & Edmonds

[57] ABSTRACT

Particular Syn (—NHCH$_3$) geometrical isomers of cyano-guanidines are disclosed as new compounds having activity as histamine antagonists useful in the treatment of gastric and duodenal ulcers.

3 Claims, No Drawings

CYANO-GUANIDINE GEOMETRICAL ISOMERS

SUMMARY OF THE INVENTION

This invention is directed to the following subjects matter:

(1) For Cyano-guanidines with the following general formula:

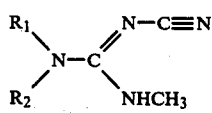    I

Distinguished by amino-ethyl and imino-nitrile tautomery and geometrical isomers (different from already-known geometrical isomers of this formula of the same tautomer form)

in which $R_1$ is an atom of Hydrogen and $R_2$ and 2-mercaptoethyl remainder;

in which $R_1$ is an atom of Hydrogen and $R_2$ is the 2-((4-methyl-5-imidazolyl)-methylthio)-ethyl remainder;

in which $R_1=R_2$ is the remainder $-CH_2-CH_2-$, the extremities of which are linked to the Nitrogen atom (aziridine remainder).

(2) Procedure for the preparation of the Syn-($-NHCH_3$) geometrical isomer (of basic nature) of the cyano-guanidine amino-ethyl and imino-nitrile tautomer having the formula:

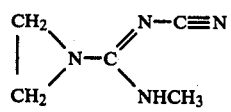    II

This preparation is characterised by the reaction of 1-(N-methyl-thio-carbamyl)-aziridine with a mercuric cyanamide in a suitable solvent, such as, for example, acetonitrile, at a temperature not over the temperature of the dimerization and the polymerization of the reacting aziridine.

(3) Procedure for the preparation of the Syn-($-NHCH_3$) geometrical isomer of the cyano-guanidine amino-methyl and imino-nitrile tautomer having the formula:

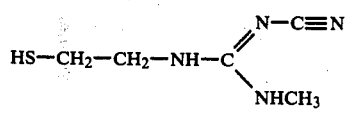    III (which geometrical isomer is different from the Anti($-NHCH_3$) isomer already known for this formula of the same tautomer form).

This preparation is characterised by the reaction, in a suitable solvent such as an alcohol or water, of the geometrical isomer of N-aziridino-N'-methyl-N''-cyano-guanidine (amino-methyl and imino-nitrile tautomer), of basic nature, with potassium or sodium terbutyl-xanthogenate. The xanthate obtained is acidolized and subsequently the hydrochloride obtained is neutralized.

(4) Procedure for the preparation of a geometrical isomer Syn($-NHCH_3$) of the cyano-guanidine (amino-methyl and imino-nitrile tautomer) having the formula:

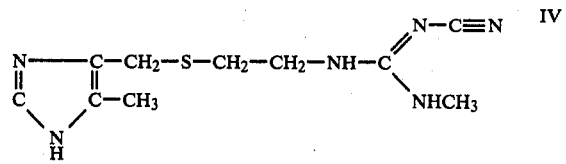    IV (which geometrical isomer is different from the Anti($-NHCH_3$) isomer already known for this formula of the same tautomer form).

This preparation is characterised by the reaction of the geometrical isomer of N-aziridino-N'-methyl-N''-cyano-guanidine (amino-methyl and imino-nitrile tautomer), of basic nature, with the hydrochloride of 4-methyl-5-mercaptomethyl-imidazole in a suitable solvent such as water and in the presence of an equally suitable alcaline agent, for example KOH and NaoH in stoichiometric quantity (as to that of the hydrochloride), plus a supplementary quantity of the said alcaline agent going from very small from the stoichiometric point of view, to for example 1/20, 1/10, 1/5, 1/1 in relation to the molar quantity of the mercapto-methyl-imidazole engaged.

From the beginning the reaction is brought about in an inert atmosphere, for example in Nitrogen or Argon. The temperature of the reaction can be from room temperature up to 100° C.

(5) Procedure for the preparation of the Syn-($-NHCH_3$) geometrical isomer of the cyano-guanidine amino-methyl and imino-nitrile tautomer with the formula:

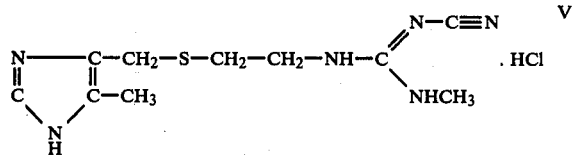    V (which geometrical isomer is different from the Anti($-NHCH_3$) isomer already known for this formula of the same tautomer form).

This preparation is charactrised by the reaction of the hydrochloride of 4-methyl-5-mercapto-methyl-imidazole with the geometrical isomer of N-aziridino-N'-methyl-N''-cyano-guanidine (amino-methyl and imino-nitrile tautomer), of basic nature, in a suitable solvent such as water, an alcohol or a chloride solvent, in an inert atmosphere, one of Nitrogen or Argon for example. The temperature can be from room temperature up to 100° C.

(6) Procedure for the preparation of the Syn-($-NHCH_3$) geometrical isomer of the cyano-guanidine amino-methyl and imino-nitrile tautomer with the formula:

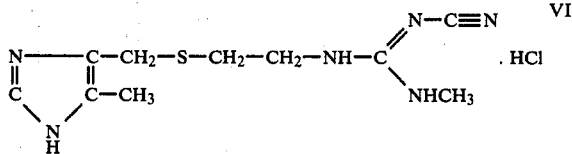    VI (which geometrical isomer would differ from any eventual Anti(—NHCH$_3$) isomer which might become known for this formula of the same tautomer form).

This preparation is characterised by the reaction of 4-methyl-5-mercapto-methyl-imidazole with the hydrochloride of the geometrical isomer of N-aziridino-N'-methyl-N''-cyano-guanidine (amino-methyl and imino-nitrile tautomer), of a basic nature, thus permitting the formation of the hydrochloride, in a solvent such as water or an alcohol, at a temperature which can go from room temperature to 100° C.

(7) Procedure for the preparation of the Syn-(—NHCH$_3$) geometrical isomer of the cyano-guanidine (amino-methyl and imino-nitrile tautomer) with the formula:

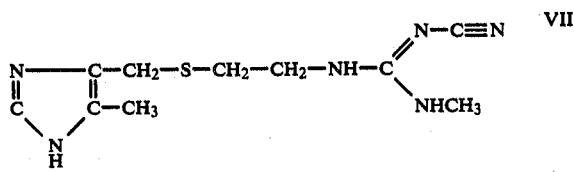

VII (which geometrical isomer is different from the Anti(—NHCH$_3$) isomer already known for this formula of the same tautomer form).

This preparation is characterised by the reaction of the hydrochloride of 4-methyl-5-chloromethyl-imidazole with the geometrical isomer of N-(2-mercapto-ethyl)-N'-methyl-N''-cyano-guanidine (amino-methyl and imino-nitrile tautomer)—which geometrical isomer is different from that already known for this formula—in a suitable solvent such as water, in the presence of an alcaline agent such as KOH, NaOH, potassium or sodium carbonate, in an inert atmosphere such as one of Nitrogen or Argon, at a temperature going from room temperature to 100° C.

(8) Procedure for the preparation of a mercuric cyanamide:

This preparation is characterised by the reaction between cyanamide and mercuric acetate in water. The precipitate formed is isolated and thoroughly dried.

(9) Procedure for the preparation of a mercuric cyanamide:

This preparation is characterised by the reaction between a solution of cyanamide in water and a suspension of mercuric chloride in water in the presence of ammonium bicarbonate or an alcaline bicarbonate. A mercuric cyanamide in a molecular form different from that of the preparation concerned in claim 8 is then isolated from the resultant precipitate.

DETAILED DESCRIPTION OF THE INVENTION

Cyano-guanidines as Tautomers and as Geometrical Isomers and their Preparation It is first necessary to define the phenomenen of geometrical isomery so as to give a dimension to the importance of the invention concerned, and secondly to describe the innovative nature of the newly-invented compounds and that of their means of preparation.

Geometrical isomery is the phenomenen of organic chemistry consisting of the asymmetry brought about by at least two different substituents being linked by two atoms, which are themselves joined by a double liaison, for example the double liaison carbon-carbon:

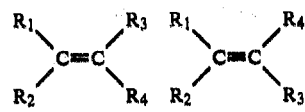

or the double liaison carbon-nitrogen:

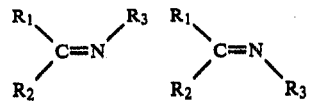

The geometrical isomers determined by the double liaison carbon-carbon and the substituents R$_1$, R$_2$, R$_3$ and R$_4$ are called cis and trans. The geometrical isomers determined by the double liaison carbon-nitrogen and the substituents R$_1$, R$_2$ and R$_3$ are called syn and anti.

Geometrical isomers can exist in pairs in the proportion of 1/1 or in other proportions according to the energy necessary to their formation (their stability). A geometrical isomer can also exist alone. Geometrical isomers can also change from one to another, for example if the double liaison disappears temporarily, making it possible for an atom of carbon or of nitrogen to rotate around the axis of the liaison Sp$^2$, either by passage through an intermediary, for example a tautomer, or through a transitional state (1), by means of a "bond-rotational mechanism" or
(2), by means of a "lateral shift mechanism":

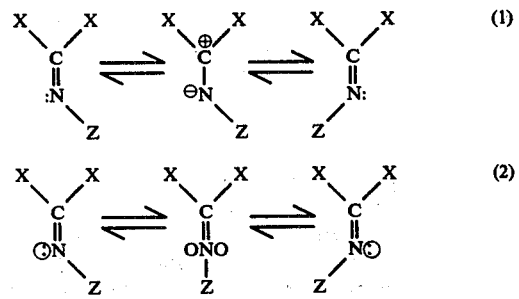

Inversions of configurations depending on a state of equilibrium and furnishing the two stable geometrical isomers, are relatively rare. To succeed in preparing the two stable geometrical isomers, it is often necessary to create a reagent which itself already possesses the desired geometrical isomer form, and to put it into contact—in order to obtain the final compound—with another suitable reagent. Thus, the existence of one geometrical isomer often does not necessarily depend on the existence of the other.

The preparation and the isolation of the two geometrical isomers of a guanidine have not yet, to our knowledge, been realised; however, on the other hand, this is not true of amidines ("Investigation of Geometrical Isomerism and tautomerism in some new Benzothiazol-2-carboxamidines", Thesis No. 1680, 1975, University of Geneva).

Thus we found that guanidines already known under one geometrical form could also exist in the other geometrical isomer form, in particular N-(2-mercapto-ethyl)-N'-methyl-N''-cyano-guanidine and N-methyl-N'-cyano-N''-[2-((4-methyl-5-imidazolyl)-methylthio)-ethyl]-guanidine. These two guanidines are of amino-methyl and imino-nitrile tautomer form.

In the particular case of the compounds we have invented, we shall consider below the particular properties which distinguish N-cyano-guanidines.

The Syn(—NHCH₃) isomer of N-cyano-guanidines of the amino-methyl and imino-nitrile tautomer form,

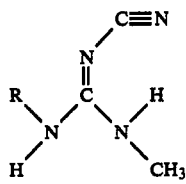   I

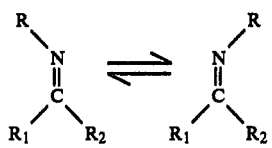

The speed of the isomerisation depends on the nature of $R_1$, $R_2$ and $R_3$. If $R=-C\equiv N$, the rapidity of the isomerisation is great and if in addition $R_1$ and $R_2$ are —NHCH₃, it will be even more so. This comes from the fact that the transitional state of the isomerisation of this guanidine requires only a small amount of energy.

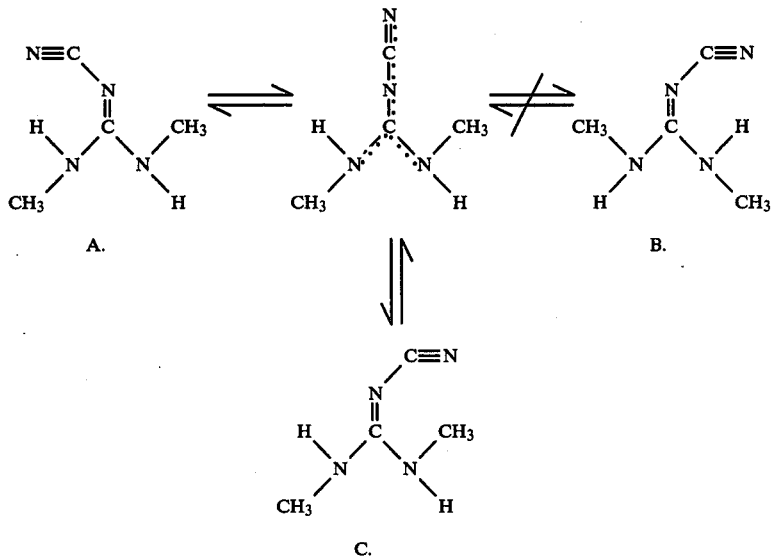

did not yet exist. This comes from the fact that the syntheses of N-cyano-guanidines carried out up to the present time only furnished anti(—NHCH₃) isomers with the formula

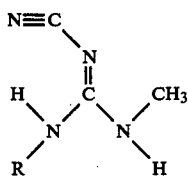   II

The cyano-guanidine of formula I and that of formula II (R being identical), in solution, are not in a state of equilibrium with one another. This is to say that from the N-cyano-guanidine of formula I one cannot obtain the N-cyano-guanidine of formula II and vice versa. An energy barrier makes the establishment of a state of equilibrium impossible. This barrier results from the rapid inversion of the group —N—C≡N and from the slower rotations of the groups —NHCH₃ and —NHR.

In fact, it is known (H. Kessler Angew, Chem. 82, n°6, 237, 1970) that imines, oximes, hydrazones and guanidines become isomers in a solution as follows:

It is to be noted that A does not furnish isomer B, but the unstable isomer C (which only exists in solution). This is due to the energy barrier evoked above, which is determined by the greater rapidity of the inversion of =N—C≡N as compared to the slower rotations of —NHCH₃.

This phenomenen is very well demonstrated by C. G. MacCarty and D. M. Wieland (Tetrahedron letters 22, 1787, 1969) in their study of the dynamic nuclear magnetic resonance of deuterized N-cyano-N',N''-methyl-guanidine, for which they determine the values: $T_c = -45°$ C., $\Delta G_c^{\ddagger}$ (Kcal/mole) = 12.3.

The isomerisation described does not result from a simultaneous inversion of =N—C≡N and the rotation of both NDCH₃ groups, for in that event, the molecules obtained, in a state of equilibrium, would be identical and the magnetic non-equivalence of the —CH₃ functions would be respected, no matter what the temperature might be.

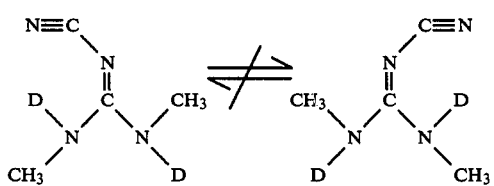

In reality, the inversion of =N—C≡N takes place more rapidly than the rotations of —NDCH₃ and the isomerisation thus furnishes a geometrical isomer which is unstable and which cannot be isolated:

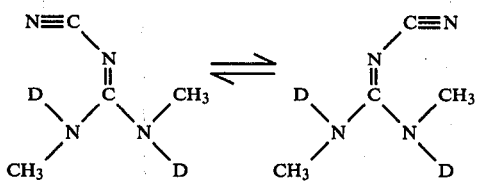

The mechanism of these isomerisations is more easily explained by "rotational-bond mechanism" than by "lateral shift mechanism"; in fact, the group

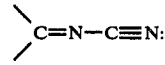

easily delocalizes two electrons, as per the following:

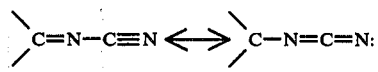

or simply in a state of transition such as

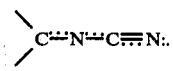

It is known that the anion —N⊖—C≡N can be stabilised by a neighbouring hetero-atom, such as sulfur, for example: R—S+—N⁻—C≡N:

The isomerisation of N-cyano-guanidines cannot at all take place through the temporary displacement of the double liaison (creating a tautomer) since the energy barrier described above is equally opposed to a tautomeric equilibrium.

Thus, the compounds of our invention, i.e., the Syn-(—NHCH₃) geometrical isomers of N-methyl-N'-cyano-N''(2-mercapto-ethyl)-guanidine and of N-methyl-N'-cyano-N'''-[2-((4-methyl-5-imidazolyl)-methylthio)-ethyl]-guanidine, (amino-methyl and imino-nitrile tautomer), with the formula:

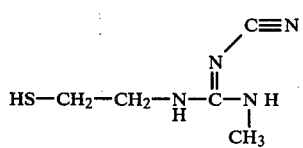

and the formula:

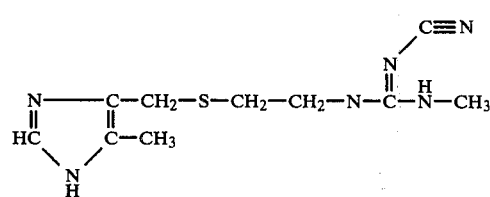

do not stem from the Anti(—NHCH₃) geometrical isomers with the same nomenclature and of the same tautomer form (i.e., as far as the compound of formula IV is concerned, they do not stem from cimetidine) following a state of equilibrium or any kind of transitional state.

The Anti(—NHCH₃) conformation of cimetidine is demonstrated by X-ray analysis (Chem. Berichte 111, 3222, 1978). From this analysis result one can conclude that the different geometrical isomer, i.e., the compound of which consists our invention as per formula IV, possesses Syn(—NHCH₃) conformation. Thus, in solution, the compounds of our invention (formulas III and IV) are in equilibrium with an unstable conformer, which it is not possible to isolate, due to the rapid inversion of —N—C≡N and the slow rotation of —NHCH₃ and —NHR:

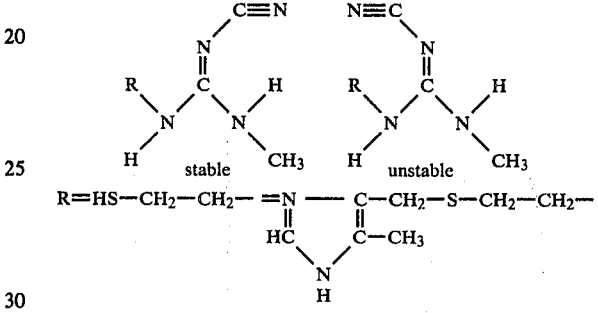

The compounds of our invention therefore have to be synthetised from an intermediary reagent which already possesses the desired Syn(—NHCH₃) isomery. This intermediary is the geometrical isomer Syn(—NHCH₃) of N-(N'-methyl-N''-cyano-amidino)-aziridine (amino-nitrile and imino-nitrile tautomer), with the formula:

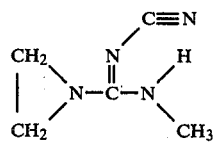

The aziridine of formula V adds the function —SH of 4-methyl-5-mercaptomethyl-imidazole, furnishing the compound of our invention as per formula IV. The aziridine of formula V adds the potassium or sodium terbutylxanthogenate, giving the compound of our invention shown in formula III.

The synthesis of the Syn(—NHCH₃) geometrical isomer of N-(N'-methyl-N''-cyano-amidino)-aziridine (amino-methyl and imino-nitrile tautomer) is accomplished sterospecifically by the action of mercuric derivates of cyanamide or by argento cyanamide's action on N-(N-methyl-thiono)-aziridine in which the thiocarbonyl function has been replaced by the imino-nitrile function.

The compound of our invention shown by formula IV can also be prepared from the reaction of the Syn-(—NHCH₃) geometrical isomer of N-methyl-N'-cyano-N''-(2-mercapto-ethyl)-guanidine (amino-methyl and imino-nitrile tautomer) of formula III, with 4-methyl-5-chloro-methyl-imidazole.

It is interesting to note that if N-(N'-methyl-thiono)-aziridine and N-(N'-methyl-N''-cyano-amidino)-aziridine are of basic nature, this probably stems from the pyramidal geometry of the nitrogen of the aziridine remainders.

Guanidines react to sodium nitroprusside with colouration (see J. P. Greenstein, M. Winitz, Chemistry of amino-acids, J. Wiley and Sons, New York-London Vol. 3, p. 1842). For example, the aziridine of formula V gives a blue colour.

The crystallisation of the compound of our invention shown by formula IV (Syn(—NHCH$_3$) geometrical isomer can be carried out in water, acetonitrile, isopropanol or in a mixture of ethanol-ether. The Syn-(—NHCH$_3$) and Anti(—NHCH$_3$) geometrical isomers of N-methyl-N'-cyano-N''-[2-((4-methyl-5-imidazolyl)-methylthio)-ethyl]-guanidine can be distinguished from one another by the following characteristics, among others:

their melting point;

the mobility in thin-layer chromatography: ($R_f$: 0.34 for Syn(—NHCH$_3$) and $R_f$: 0.29 for Anti(—NHCH$_3$), n-butanol-ac, acetic-water 10/2/5 v;

deposited on a plate of silica gel 60 F 254 or after chromatography on the same silica, with nitroprusside as reagent, the Syn(—NHCH$_3$) isomer causes a sky-blue colouration and the Anti(—NHCH$_3$) isomer a rose colouration.

The compound of our invention consisting of the Syn(—NHCH$_3$) geometrical isomer of formula IV and the salts of this compound which are suitable for therapeutical use, as well as the various polymorphous crystalline forms in which this geometrical isomer can exist, act as histamine antagonists at the receptors called H$_2$, by which histamine stimulates the production of gastric hydrochloric acid at the parietal cells.

The compound of our invention consisting of the Syn(—NHCH$_3$) geometrical isomer of formula IV and the salts of this compound which are suitable for therapeutical use can be used in the treatment of gastric and duodenal ulcer.

The compound of the invention consisting of the geometrical isomer Syn(—NHCH$_3$) of formula IV, presents over the Anti(—NHCH$_3$) geometrical isomer of the same formula, the advantage of a better bio-availability due to better solubility of the crystals, probably thanks to different intra-molecular hydrogen liaisons.

Examples of excipients which are suitable for the pharmaceutical form are: lactose, saccharose, talc, gelatin, gomme arabique, olive oil.

EXAMPLE 1

N-aziridino-N'-methyl-N''-cyano-guanidine (amino-methyl and imino-nitrile tautomer, geometrical isomer of basic nature)

To a solution of 3.8 gms. 1-(N-methyl-thiocarbamyl)-aziridine (F. 46° C.) in acetonitrile cooled in ice are added 7.4 gms. of a mercuric cyanamide and the reaction is left under agitation, during the first 10 hours in ice, then up to the 28th hour, under normal temperature.

The part still not dissolved is filtered (this gives a neutral yellow powder, with an IR(nujol) of 2030, 1930 cm$^{-1}$. The filtrate is kept at low temperature, which provokes the precipitation of a yellow amorphous substance. After filtration, the solvent is eliminated in vacuum at 0.05 T and at a temperature not over 40° C. One thus obtains an oil having a marked basic nature, with the following characteristics:

It becomes partially polymerised in acetic acid in the presence of perchloric acid:

$R_f$: 0.75 silica GF (chloroform-methanol 9/1 vol);

A light blue colouration appears after deposit on a plate of silica with the reagent sodium nitroprusside;

Titration with S$_2$O$_3$N$_{a2}$ (Ann. Chem. 27, 540, 1955): 98.2%;

IR (film): 3220, 3040, 2980, 2900, 2160, 1600, 1545, 1440, 1410, 1360, 1375, 1190, 1150, 1070, 1010, 930, 880, 850, 810-805 cm$^{-1}$.

EXAMPLE 2

Mercuric cyanamide (Compound A)

To a solution of 31.86 gms. of mercuric acetate in 80 ml. water, a solution of 4.2 gms. cyanamide in 10 ml. of water is added. The suspension formed is allowed to separate. The concentrate thus obtained is then centrifuged out, washed with water and dried under vacuum at 0.5 T. This gives a white powder very slightly soluble in organic solvents as well as in water:

Hg: 95.8% of the theoretical value;

IR (nujol): 2080, 2030 and 1930 cm $^{-1}$.

(Compound B)

To a suspension of 27.1 gms. mercuric chloride in 250 ml. of water, 9 gms. Cyanamide and 15.8 gms. of ammonium bicarbonate are added. After three hours under agitation, the solution is filtered, the filtrate washed with water and dried under vacuum at 0.5 T. This gives a white powder, very slightly soluble in water and the organic solvents:

Hg: 96.3%;

IR (nujol): 2100, 1210 cm$^{-1}$.

EXAMPLE 3

Syn(—NHCH$_3$) geometrical isomer of N-methyl-N'-cyano-N'' [2((4-methyl-5imidazolyl)-methylthio)-ethyl)]-guanidine (amino-methyl and imino-nitrile tautomer)

To a solution of 16.45 gms. hydrochloride of 4-methyl-5-mercapto-methyl-imidazole in 110 ml. of NaOH 1N, under a Nitrogen or Argon current, is added a solution of 12.6 gms. N-aziridino-N'-methyl-N''-cyano-guanidine (amino-methyl and imino-nitrile tautomer, geometrical isomer of basic nature).

Condensation is carried out at normal temperature, in an inert atmosphere, during 15 hours. A small insoluble fraction centrifuges out, the remaining solvent is evaporated under a vacuum of 0.02 T and the residue is taken up by acetonitrile. The NaCl is eliminated and the product is crystallised at, for example, −5° C.

$R_f$: 0.54 (0.34 with the same solvent freshly prepared) (silica GF, n-butanol-acetic acid-water 10/ 2/5 vol);

Sky-blue colouration appears upon deposit on a silica GF plate with sodium nitroprusside as reagent;

IR (nujol): 3200, 3070, 2160, 1620, 1580, 1518. 1690, 1420, 1340, 1305, 1280, 1260, 1235, 1220, 1200, 1155, 1070, 950, 845, 775, 700, 670, 630 cm$^{-1}$;

F. 120°-122° C.;

C$_{10}$H$_{16}$N$_6$S (252) Calc. C 47. 61, H 6.35, N 33. 33, S 12.64%; Tr. C 47. 53, H 6.51, N 33. 37, S 12.58%

EXAMPLE 4

Syn(—NHCH₃) geometrical isomer of N-methyl-N'-cyano-N''-(2-mercapto-ethyl)-guanidine (amino-methyl and imino-nitrile tautomer)

To a solution in water of 12.4 gms. Syn(—NHCH₃) geometrical isomer of N-aziridino-N'-methyl-N''-cyano-guanidine (amino- methyl and imino-nitrile tautomer) is added 15.8 gms. of potassium terbutylxanthogenate. After 8 hours of reaction at room temperature, this solution is neutralised, the solvent is eliminated and the crystalline residue is taken up by a solution of HCl in ethanol. After 3 hours, at room temperature, the product is isolated in the form of a hydrochloride:
Titration sodium methoxyde: 99.4%;
A red colouration is obtained upon treatment with a "spray" of nitroprusside reagent. This effect is immediately evident.

EXAMPLE 5

Syn (—NHCH₃) geometrical isomer of N-methyl-N'-cyano-N''-[2-((4-methyl-5-imidazolyl)-methylthio)-ethyl)]-guanidine (amino-methyl and imino-nitrile tautomer)

To a solution of 2.66 gms. N-methyl-N'-cyano-N''-(2-mercapto-ethyl)-guanidine and 2.77 gms. hydrochloride of 4-methyl-5-chloro-methyl-imidazole in water, 1.85 gms. KOH are added under Nitrogen current. The temperature of the reaction is brought up to 50° C. and a pH of 11 maintained.

After 5 hours the solvent is eliminated under a vacuum at 0.02 T. The residue is taken up with acetonitrile, the KCl is eliminated and the product crystallised at −10° C.
F. 120°—122° C.
analysis results as in example 3.

EXAMPLE 6

Hydrochloride of Syn(—NHCH₃) geometrical isomer of N-methyl-N'-cyano-N''-[2((4-methyl-5-imidazolyl)-methylthio)-ethyl)]-guanidine (amino-methyl, imino-nitrile tautomer)

To a solution of 12.4 gms. N-aziridino-N'-methyl-N''-cyano-guanidine in a Nitrogen atmosphere, add 16.4 gms. Hydrochloride of 4-methyl-5-mercapto-methyl-imidazole. After 17 hours at room temperature, the solvent is evaporated under vacuum at 0.02 T and the hydrochloride is crystallised in ethanol by use of ether.

I claim:
1. The substantially pure Syn(—NHCH₃) geometrical isomer having the structure

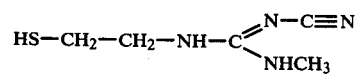

on a therapeutically acceptable acid addition salt thereof.

2. The substantially pure Syn(—NHCH₃) geometrical isomer of the structure

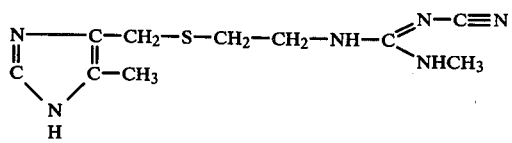

having a melting point of 120°–122° C. on a therapeutically acceptable acid addition salt thereof.

3. The basic substantially pure Syn(—NHCH₃) geometrical isomer of the structure.

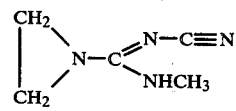

* * * * *